(12) United States Patent
Murakawa et al.

(10) Patent No.: US 11,312,991 B2
(45) Date of Patent: Apr. 26, 2022

(54) METHOD FOR DECODING BASE SEQUENCE OF NUCLEIC ACID CORRESPONDING TO END REGION OF RNA AND METHOD FOR ANALYZING DNA ELEMENT

(71) Applicant: KABUSHIKI KAISHA DNAFORM, Yokohama (JP)

(72) Inventors: Yasuhiro Murakawa, Saitama (JP); Yujiro Takegami, Kanagawa (JP)

(73) Assignee: KABUSHIKI KAISHA DNAFORM, Kanagawa (JP)

( * ) Notice: Subject to any disclaimer, the term of this patent is extended or adjusted under 35 U.S.C. 154(b) by 437 days.

(21) Appl. No.: 16/073,210

(22) PCT Filed: Jan. 13, 2017

(86) PCT No.: PCT/JP2017/001097
§ 371 (c)(1),
(2) Date: Jul. 26, 2018

(87) PCT Pub. No.: WO2017/130750
PCT Pub. Date: Aug. 3, 2017

(65) Prior Publication Data
US 2019/0032127 A1    Jan. 31, 2019

(30) Foreign Application Priority Data

Jan. 27, 2016  (JP) .............................. JP2016-013575

(51) Int. Cl.
| C12Q 1/68 | (2018.01) |
| C12Q 1/6869 | (2018.01) |
| C12N 15/10 | (2006.01) |
| C12N 15/113 | (2010.01) |
| C12Q 1/6806 | (2018.01) |
| C12Q 1/686 | (2018.01) |
| C07H 21/04 | (2006.01) |
| C07H 21/00 | (2006.01) |

(52) U.S. Cl.
CPC ....... *C12Q 1/6869* (2013.01); *C12N 15/1096* (2013.01); *C12N 15/113* (2013.01); *C12Q 1/68* (2013.01); *C12Q 1/6806* (2013.01); *C12Q 1/686* (2013.01); *C12N 2310/11* (2013.01)

(58) Field of Classification Search
None
See application file for complete search history.

(56) References Cited

U.S. PATENT DOCUMENTS

| 5,695,934 A | 12/1997 | Brenner |
| 5,962,272 A | 10/1999 | Chenchik et al. |
| 6,013,488 A | 1/2000 | Hayashizaki |
| 6,022,715 A | 2/2000 | Merenkova et al. |
| 6,265,163 B1 | 7/2001 | Albrecht et al. |
| 6,280,935 B1 | 8/2001 | Macevicz |
| 6,306,597 B1 | 10/2001 | Macevicz |
| 6,352,828 B1 | 3/2002 | Brenner |
| 2002/0106666 A1 | 8/2002 | Hayashizaki |
| 2005/0250100 A1 | 11/2005 | Hayashizaki et al. |
| 2015/0184246 A1* | 7/2015 | Berger ................ C12Q 1/6886 514/19.6 |

FOREIGN PATENT DOCUMENTS

| JP | 2005-535311 | 11/2005 |
| JP | 2009-072062 | 4/2009 |
| WO | 03/106672 | 12/2003 |
| WO | 2007/117039 | 10/2007 |

OTHER PUBLICATIONS

Magnuson et al., "Identifying transcription start sites and active enhancer elements using BruUV-seq", Scientific Reports, 5:17978, Dec. 2015, 1-12. (Year: 2015).*
Murata et al., "Detecting Expressed Genes Using CAGE", Methods in Molecular Biology, 2014, vol. 1164, pp. 67-84. (Year: 2014).*
Shiraki et al., "Cap analysis gene expression for high-throughput analysis of transcriptional starting point and identification of promoter usage", Proceedings of the National Academy of Sciences of the United States of America., vol. 100, No. 26, p. 15776-15781, 2003.
Andersson et al., "An atlas of active enhancers across human cell types and tissues", Nature, vol. 507, No. 7493, pp.455-461, 2014.
Wuarin et al., "Physical Isolation of Nascent RNA Chains Transcribed by RNA Polymerase II: Evidence for Cotranscriptional Splicing", Molecular and Cellular Biology, vol. 14, No. 11, pp. 7219-7225, 1994.
Murata et al., "Detecting Expressed Genes Using CAGE", Methods in Molecular Biology., vol. 1164, pp. 67-85, 2014.

(Continued)

*Primary Examiner* — Bradley L. Sisson
(74) *Attorney, Agent, or Firm* — Hamre, Schumann, Mueller & Larson, P.C.

(57) ABSTRACT

The present invention provides an analysis method by which a DNA element can be identified with higher sensitivity, and a transcription amount of the DNA element can be determined. The present invention is a method for decoding a base sequence of a nucleic acid corresponding to an end region of RNA, including: a preparing-decoding step of preparing, using a template RNA, at least one nucleic acid selected from the group consisting of: an RNA nucleic acid of a 5'-end region of the template RNA or a complementary DNA nucleic acid corresponding to the 5'-end region of the template RNA; an RNA nucleic acid of 3'-end region of the template RNA or a complementary DNA nucleic acid corresponding to the 3'-end region of the template RNA; an RNA nucleic acid of a partial region of an antisense strand or a sense strand for a full length of the template RNA; and combinations thereof or a nucleic acid having a sequence that has two or more linked sequences thereof, wherein the template RNA to be used in the preparing-decoding step is a nascent RNA. The DNA element can be identified and analyzed with higher accuracy and higher sensitivity by determining information on the decoded sequence of the nucleic acid and mapping the DNA element to the genome.

13 Claims, 4 Drawing Sheets

(56) References Cited

OTHER PUBLICATIONS

Plessy et al., "Linking promoters to functional transcripts in small samples with nanoCAGE and CAGEscan", Nature Methods, vol. 7, No. 7, pp. 528-534, 2010.

Kanamori-Katayama et al., "Unamplified cap analysis of gene expression on a single-molecule sequencer", Genome Research, vol. 21, No. 7, pp. 1150-1159, 2011.

Piero Caminci et al., "High-efficiency full-length cDNA cloning by Biotinylated CAP Trapper", GENOMICS, vol. 37, pp.327-336, 1996.

Maruyama, et al., "Oligo-capping: a simple method to replace the cap structure of eukaryotic mRNAs with oligoribonucleotides", Gene, vol. 138, Issu.1-2, pp. 171-174, 1994.

Edery et al., "An Efficient Strategy to Isolate Full-Length cDNAs Based on an mRNA Cap Retention Procedure (CAPture)", Molecular and Cellular Biology, vol. 15, No. 6, pp. 3363-3371, 1995.

Theissen et al., "Cloning of the human cDNA for the U1 RNA-associated 70K protein", The EMBO Journal., vol. 5 No. 12, pp. 3209-3217, 1986.

Carninci et al., "Extra-Long First-Strand cDNA Synthesis", BioTechniques, vol. 32, No. 5, pp. 984-985, 2002.

Y. Shibata et al., "Cloning Full-Length, Cap-Trapper-Selected cDNAs by Using the Single-Strand Linker Ligation Method", BioTechniques, vol. 30, No. 6, pp. 1250-1254, 2001.

Velculescu et al., "Serial Analysis of Gene Expression", Science, vol. 270, Issu.5235, pp. 484-487, 1995.

Suzuki et al., "Diverse transcriptional initiation revealed by fine, large-scale mapping of mRNA start sites", EMBO reports, vol. 2, No. 5, pp. 388-393, 2001.

Suzuki et al., "Identification and characterization of the Potential Promoter Regions of 1031 Kinds of Human Genes", Genome Research, vol. 11, No. 5, pp. 677-684, 2001.

Core et al., "Analysis of nascent RNA indentifies a unified architecture of initiation regions at mammalian promoters and enhancers", Nature Genetics, vol. 46, No. 12, pp. 1311-1320, 2014.

Magnuson et al., "Identifying transcription start sites and active enhancer elements using BruUV-seq", Scientific Reports, No. 5:17978, pp. 1-12, 2015.

Lam et al., "Enhancer RNAs and regulated transcriptional programs", Trends in Biochemical Sciences, vol. 39, No. 4, pp. 170-182, 2014.

Kodzius et al., "CAGE: cap analysis of gene expression". Nature Methods, vol. 3, No. 3 pp. 211-222, 2006.

Murakawa et al., "Enhanced Identification of Transcriptional Enhancers Provides Mechanistic Insights into Diseases", Trends in Genetics, vol. 32, No. 2, pp. 76-88, 2016.

Mayer et al., "Native Elongating Transcript Sequencing Reveals Human Transcriptional Activity at Nucleotide Resolution", Cell, vol. 161, pp. 541-554, 2015.

Cai et al., "Transcription Initiation by RNA Polymerase II in Vitro", The Journal of Biological Chemistry, vol. 262, No. 1, pp. 298-304, 1987.

Extended European Search Report in the corresponding European Patent Application No. 17743981.7 dated Jun. 4, 2019, 11 pages.

Kruesi William S et al., "Condensin controls recruitment of RNA polymerase II to achieve nematode X-chromosome dosage compensation", ELIFE Jun. 18, 2013, pp. 1-31, vol. 2, Jun. 18, 2013 (Jun. 18, 2013), p. e00808, ISSN:2050-084X.

Yuzuki Manabe, "Sequencing Guide of nAnT-iCAGE Library with an Illumina 2000/2500 Sequencer", Manual K.K. DNAFORM, CAGE Library Sequencing Guide, Jun. 27, 2014 (Jun. 27, 2014), pp. 1-7, Retrieved from the Internet: URL:http://cage-seq.com/pdf/sequencing-guide-of-cage-library-with-an-illumina-2000.pdf [retrieved on May 14, 2019].

Takahashi Hazuki et al., "5' end-centered expression profiling using cap-analysis gene expression and next generation sequencing", Nature Protocols Feb. 23, 2012, vol. 7, No. 3, Feb. 23, 2012 (Feb. 23, 2012), pp. 542-561, ISSN: 1750-2799.

Hashimoto Shin-Ichi et al., "5'-end SAGE for the analysis of transcriptional start sites", Nature Biotechnology, Gale Group Inc, New York, vol. 22, No. 9, Sep. 1, 2004 (Sep. 1, 2004), pp. 1146-1149, ISSN: 1087-0156, DOI: 10.1038/NBT998.

Cvetesic Nevena et al., "SLIC-CAGE: high-resolution transcription start site mapping using nanogram-levels of total RNA", Genome Research 12 2018, vol. 28, No. 12, Dec. 2018 (Dec. 2018), pp. 1943-1956, ISSN: 1549-5469.

\* cited by examiner

METHOD FOR DECODING BASE SEQUENCE OF NUCLEIC ACID CORRESPONDING TO END REGION OF RNA AND METHOD FOR ANALYZING DNA ELEMENT

TECHNICAL FIELD

The present invention relates to a method for decoding a base sequence of a nucleic acid corresponding to an end region of RNA and a method for analyzing a DNA element.

BACKGROUND ART

In elucidation of biological events of diseases, the involvement of variation in control of gene expression is suggested. To elucidate the variation, analysis of gene expression profile is really important. The gene expression profile is information on, for example, genes that express, sites (e.g., cells, tissues) in biological bodies at which the gene expression occurs, the timing at which the gene expression occurs, and the behavior of the gene expression.

As a method for analyzing the expression profile, CAGE (Cap Analysis Gene Expression) has been reported at this time (Patent Literature 1, Non-Patent Literature 1). The CAGE is a method in which each base of the 5'-end region of RNA transcribed from a gene (DNA) is genome-widely identified and quantitatively determined using a cap structure at the capped 5' end. Specifically, the 5'-end region of the transcribed RNA is taken out as a cDNA tag that is obtained by reverse transcription of the 5'-end region, and a sequence of the obtained cDNA tag is determined, and thus, for example, a functional DNA element such as a promoter can be mapped in the genome. Moreover, when the sequence of an overlapping cDNA tag is determined and is mapped, an expression level of each DNA element can be measured from the number of the tags mapped at the same position. As described above, the CAGE can genome-widely analyze expression profiles and thus is promoted to be used in, for example, elucidation of causes of diseases, methods for diagnosing diseases, and methods for treating diseases.

There is an enhancer as a DNA element that is an object of the analysis of the above-mentioned expression profile. The enhancer is present in an upstream region, a downstream region, or the inside of the gene and is a cis-regulatory DNA region that has an action of increasing the gene expression and has a base length of hundreds of bases. Moreover, it is pointed out that the enhancer is involved in various diseases. Thus, it is really important to analyze the expression profile of the enhancer that is considered to play an important role in biological events.

As to enhancers, it has been reported that RNA (hereinafter referred to as "enhancer RNA") is bidirectionally synthesized from both ends of the enhancer by recruiting a general transcription factor or RNA polymerase. It has also been revealed that the enhancer RNA has a 5'-end cap structure as in mRNA. Hence, the analysis of the enhancer using CAGE that uses the 5'-end cap structure has progressed, a transcription start site of the enhancer RNA is identified, and identification of about 44000 sites of enhancer (hereinafter referred to as the "active enhancer") transcribed on the basis of the identified transcription start site has been reported (Non-Patent Literature 2).

CITATION LIST

Patent Literature

Patent Document 1: JP 2005-535311 A

Non Patent Literatures

Non-Patent Document 1: Shiraki et al., Proc. Natl. Acad. Sci. USA 100, 15776-15781 (2003)
Non-Patent Document 2: Andersson et al., Nature 507(7493) 455-461(2014)

SUMMARY OF INVENTION

Technical Problem

However, the inventors of the present invention found a novel problem in analysis of enhancers by the CAGE.

First, even when enhancer RNA that is an RNA product of enhancer is synthesized (transcribed), the enhancer RNA is actively degraded. Thus, in the case of using a sample derived from a single cell strain of a subject, enhancer RNA to be determined is merely a small portion of the entire enhancer RNA transcribed in the cell, and it is difficult to perform sensitive identification. In contrast, in the non-patent literature 2, a transcription start site is identified using total RNA in the cell, the enhancer accumulates about 1000 kinds of enormous CAGE data obtained from cells and tissues, and tens of thousands of sites such as mentioned above are identified by comprehensively analyzing these accumulated data. However, since enormous CAGE data obtained from various cells and tissues are used, the sensitivity of the identification of the "site" at which enhancer RNA is expressed, which is important in the expression profile might be insufficient. Specifically, since an association between mutation of enhancer and canceration in the cancer subject is suggested, it is important that an enhancer is identified not from the accumulated CAGE data of various cells and tissues but from only a single sample in the medical field.

The enhancer RNA is synthesized and degraded in parallel. Thus, the expression level of the detected enhancer RNA is merely an apparent expression level based on the equilibrium between the synthetic amount and the degradation amount. Therefore, for example, the change in the expression level of the enhancer RNA over time and the absolute amount of the expression level cannot be determined. However, in analysis of the expression profile, it is important to determine the absolute amount of the synthesis of the enhancer RNA to determine enhancer activity.

This problem is involved in not only the enhancer, but also, for example, many protein-noncoding RNAs (ncRNAs) that are degraded actively as in the case of the enhancer and RNAs that encode protein known as a regulatory factor such as a transcription factor.

Hence, the present invention is intended to provide a method for encoding a base sequence of a nucleic acid corresponding to an end region of an RNA and a method for analyzing a DNA element, to identify, for example, a functional DNA element such as an enhancer with higher sensitivity and quantify the activation of the functional DNA element with higher accuracy.

Solution to Problem

In order to achieve the aforementioned object, the present invention provides a method for decoding a base sequence of a nucleic acid corresponding to an end region of RNA (hereinafter also referred to as "the decoding method of the present invention"), including: a preparing-decoding step of preparing, using a template RNA, at least one nucleic acid selected from the group consisting of: an RNA nucleic acid of a 5'-end region of the template RNA or a complementary DNA nucleic acid corresponding to the 5'-end region of the template RNA; an RNA nucleic acid of 3'-end region of the template RNA or a complementary DNA nucleic acid corresponding to the 3'-end region of the template RNA; an RNA nucleic acid of a partial region of a sense strand or an antisense strand for a full length of the template RNA; and combinations thereof or a nucleic acid having a sequence that has two or more linked sequences thereof, wherein the template RNA to be used in the preparing-decoding step is a nascent RNA.

The present invention further provides a method for analyzing a DNA element (hereinafter also referred to as "the analysis method of the present invention"), including: a decoding step of decoding a base sequence of a nucleic acid corresponding to an end region of an RNA by the decoding method of the present invention, a decoding step of decoding the base sequence of a nucleic acid corresponding to an end region of an RNA, and a mapping step of mapping of a DNA element that encodes synthesis of the RNA to a genome sequence on the basis of decoded sequence information.

Advantageous Effects of Invention

The present invention can identify, for example, a functional DNA element such as an enhancer with higher sensitivity and can determine the transcription amount of the functional DNA element.

DESCRIPTION OF EMBODIMENTS

For example, in the preparing-decoding step of the decoding method of the present invention, the nucleic acid to be prepared includes at least one of the RNA nucleic acid of the 5'-end region of the template RNA or the complementary DNA nucleic acid corresponding to the 5'-end region of the template RNA, and a technique based on nAnT-iCAGE method is used.

For example, in the preparing-decoding step of the decoding method of the present invention, the nucleic acid to be prepared includes at least one of the RNA nucleic acid of the 5'-end region of the template RNA or the complementary DNA nucleic acid corresponding to the 5'-end region of the template RNA, and the preparing-decoding step includes: a preparing step of preparing a linker-added nucleic acid having a linker bound to the nucleic acid; a cleaving step of cleaving the linker-added nucleic acid using a restriction enzyme having a recognition site in the linker and a cleavage site in the nucleic acid, and a collecting step of collecting a fragment corresponding to the 5'-end region of the template RNA from the obtained cleavage product.

For example, in the preparing-decoding step of the decoding method of the present invention, the nucleic acid to be prepared includes at least one of the RNA nucleic acid of the 5'-end region of the template RNA or the complementary DNA nucleic acid corresponding to the 5'-end region of the template RNA, and a technique based on template switching method is used.

For example, in the preparing-decoding step of the decoding method of the present invention, the nucleic acid to be prepared includes at least one of the RNA nucleic acid of the 5'-end region of the template RNA or the complementary DNA nucleic acid corresponding to the 5'-end region of the template RNA, and a technique based on HeliScopeCAGE method is used.

For example, in the decoding method of the present invention, the nascent RNA is derived from a single cell strain or a single tissue.

For example, in the decoding method of the present invention, the nascent RNA is isolated from a complex of a template DNA and an RNA polymerase II in transcription and an RNA during synthesis.

For example, the decoding method of the present invention further includes: an isolating step of isolating the nascent RNA from a biological sample, and the isolated nascent RNA is used as the template RNA.

For example, in the isolating step of the decoding method of the present invention, chromatin containing a complex of a template DNA and an RNA polymerase II in transcription and an RNA during synthesis is isolated from the biological sample, and an RNA in synthesis contained in the complex is isolated from the chromatin as a nascent RNA.

For example, in the mapping step of the analysis method of the present invention, DNA element is identified by the mapping.

For example, the analysis method of the present invention further includes a step for determining an activity level of the DNA element from the number of overlapping portions of the mapped DNA fragment.

For example, in the analysis method of the present invention, the determined activity level of the DNA element is associated with at least one of a DNA mutation or a polymorphism in the genome.

The following describes the present invention in detail. The present invention, however, is by no means limited thereto.

(Decoding Method)

The decoding method of the present invention is a method for decoding a base sequence of a nucleic acid corresponding to an end region of RNA, including: a preparing-decoding step of preparing, using a template RNA, at least one nucleic acid selected from the group consisting of: an RNA nucleic acid of a 5'-end region of the template RNA or a complementary DNA nucleic acid corresponding to the 5'-end region of the template RNA; an RNA nucleic acid of 3'-end region of the template RNA or a complementary DNA nucleic acid corresponding to the 3'-end region of the template RNA; an RNA nucleic acid of a partial region of an antisense strand or a sense strand for a full length of the template RNA; and combinations thereof or a nucleic acid having a sequence that has two or more linked sequences thereof, wherein the template RNA to be used in the preparing-decoding step is a nascent RNA. In the present invention, the nucleic acid to be prepared can also be referred to as, for example, a nucleic acid fragment or a fragment, and when the nucleic acid to be prepared is a DNA nucleic acid, the nucleic acid can also be referred to as a DNA fragment.

Specifically, in the decoding method of the present invention, the nucleic acid is prepared using a nascent RNA, i.e., an RNA during novel synthesis in the transcription as a template RNA, and the sequence of the nucleic acid is decoded. Thus the method has the following effects in analysis of the DNA element.

First, as mentioned above, for example, in the case of the enhancer, the enhancer RNA after the completion of synthesis is actively degraded. However, in the decoding method of the present invention, not the RNA after the completion of synthesis, but a nascent RNA during novel synthesis is used as a template. Thus, for example, not a nucleic acid corresponding to an RNA that shows an equilibrium relationship between synthesis and degradation and thus is apparently present, but a nucleic acid corresponding to an RNA before degradation, i.e., an nucleic acid corresponding to an RNA that is not an apparent RNA but is actually synthesized can be obtained. Therefore, for example, in the case of analysis of DNA element such as an enhancer in a single cell strain or a single tissue, identification can be performed with higher sensitivity.

A nucleic acid corresponding to an actually synthesized RNA can be obtained. Not the apparent RNA amount showing an equilibrium state between synthesis and degradation, but the amount of synthesized RNA can be measured. Thus, it can be said that an absolute quantitative determination can be substantially performed. Therefore, for example, in the case of the DNA element such as an enhancer, an absolute quantitative determination of DNA element activity such as enhancer activity can be indirectly performed by the absolute quantitative determination of the transcribed RNA.

As described above, the present invention can perform identification of unknown DNA element and quantitative determination of activity of the unknown DNA element or identification of DNA element in a single cell strain or a single tissue and quantitative determination of activity of the DNA element can be performed with higher sensitivity and higher accuracy.

The "nascent RNA" means an RNA during novel synthesis in transcription using DNA as a template.

The nascent RNA is, for example, RNA included in a complex of a template DNA and RNA polymerase II in transcription and RNA during synthesis, and RNA (RNA during synthesis) isolated from the complex can be used.

The nascent RNA is, for example, RNA having a 5'-end cap structure (hereinafter also referred to as the "5' cap structure") by capping the 5' end in transcription.

A method for preparing the nascent RNA is not limited to particular methods. As the method, for example, a document of Jerome Wuarin et al. (Molecular and Cellular Biology, Nov. 1994, p. 7217-7225) can be used as reference.

A sample for preparing the nascent RNA is, for example, a biological sample. The kind of the biological sample is not limited to particular kinds, and examples thereof include cells and tissues. The cells can be one kind of cells or a mixture of two or more kinds of cells. The tissues can be, for example, one kind of tissues or a mixture of two or more kinds of tissues. The present invention can also be used in analysis of DNA element in a single cell strain or single tissue because a DNA fragment that is not affected by degradation of RNA as mentioned above. Thus, in the present invention, for example, one kind of cells (single cell strain) or one kind of tissue (single tissue) are preferably used as the biological sample.

The kind of the cells is not limited to particular kinds, and any kind of cells can be used. By performing the analysis method of the present invention using the DNA fragment obtained by the decoding method of the present invention, a DNA element that is involved in diseases can be analyzed, for example. Specific examples of the kind of the cells include blood cells, lymphoblastoid cells, and tumor cells.

The nascent RNA can be prepared as follows, for example. First, a nuclear fraction containing a nucleus is separated from cells by a usual method. Subsequently, the nuclear fraction is denatured to separate a chromatin fraction. The chromatin fraction contains a complex of a template DNA and an RNA polymerase II in transcription and an RNA during synthesis. The complex is really stable, and the structure thereof is thus maintained after the denaturation. For the denaturation, a denaturation buffer containing a salt and urea at high concentrations can be used, for example. The composition of the denaturation buffer can be, for example, as follows: 300 mmol/L salt, 4 mol/L urea, 1% surfactant. The salt can be, for example, sodium chloride, and the surfactant can be, for example, a nonionic surfactant such as NP-40 (Nonidet P-40). Then, the chromatin fraction is subjected to RNA extraction to collect RNA during synthesis contained in the complex. The collected RNA is the nascent RNA. For the RNA extraction, a commercially available RNA extraction reagent can be used, for example, and as the commercially available RNA extraction, a Trizol (registered trademark) RNA isolation reagent can be used, for example.

The decoding method of the present invention may further include, for example, an isolating step of isolating the nascent RNA from a biological sample. The nascent RNA isolated in the isolating step may be used as the template RNA. The isolating step can be performed by, for example, separating chromatin containing a complex of a template DNA and an RNA polymerase II in transcription and an RNA during synthesis from the biological sample and separating, as nascent RNA, RNA during synthesis contained in the complex from the chromatin. As a method for isolating the nascent RNA, the above-mentioned method for preparing the nascent RNA can be used, for example.

In the decoding method of the present invention, the nucleic acid to be prepared includes the following nucleic acids (1) to (4) and may be the following nucleic acid (5):
(1) an RNA nucleic acid of the 5'-end region of the RNA or a complementary DNA nucleic acid corresponding to the 5'-end region of the RNA;
(2) an RNA nucleic acid of 3'-end region of the RNA or a complementary DNA nucleic acid corresponding to the 3'-end region of the RNA;
(3) an RNA nucleic acid of a partial region of an antisense strand or a sense strand in a full length of the RNA;
(4) any combination of the nucleic acids (1) to (4);
(5) a nucleic acid having a sequence obtained by linking at least two sequences with each other. In the nucleic acid (5), the "sequences" in the "at least two sequences" are at least two sequences among the sequences of the nucleic acids (1) to (4), and the "sequence obtained by linking at least two sequences with each other" is a sequence obtained by linking at least two sequences among the sequences of the nucleic acids (1) to (4) with each other. The linkage may not be direct linking and may be indirect linking via a linker, for example.

When the nucleic acid to be prepared in the preparing-decoding step of the decoding method of the present invention includes an RNA nucleic acid of the 5'-end region of the template RNA or a complementary DNA nucleic acid corresponding to the 5'-end region of the template RNA, various methods based on the principle of CAGE can be used in the preparing-decoding step, for example. The nucleic acid may be, for example, an RNA nucleic acid of the 5'-end region of the template RNA or a complementary DNA nucleic acid to the 5'-end region of the RNA or may include both of the RNA nucleic acid of the 5'-end region of the template RNA and the complementary DNA nucleic acid to the 5'-end region of the RNA.

In this case, the nucleic acid prepared using the nascent RNA as a template is not a nucleic acid corresponding to the 3'-end region of the nascent RNA but a DNA fragment corresponding to the 5'-end region of the nascent RNA. Thus, for example by determining information on the sequence of the DNA fragment, information on the sequence of the 5'-end region of the nascent RNA, i.e., information on the sequence from the transcription start site can be determined. Therefore, for example, genome-wide identification of the DNA element, i.e., identification of the position of the DNA element in the genome can be performed with higher accuracy. Accordingly, for example, a functional DNA element such as an unknown enhancer can be identified.

When the nucleic acid to be prepared in the preparing-decoding step of the decoding method of the present invention includes an RNA nucleic acid of the 5'-end region of the template RNA or a complementary DNA nucleic acid corresponding to the 5'-end region of the template RNA, a technique based on the nAnT-iCAGE method can be used in the preparing-decoding step, for example. The nAnT-iCAGE method is not particularly limited, and, for example, Murata et al., 2014 Methods Mol Biol. 1164 67-85 can be referenced.

When the nucleic acid to be prepared in the preparing-decoding step of the decoding method of the present invention includes an RNA nucleic acid of the 5'-end region of the template RNA or a complementary DNA nucleic acid corresponding to the 5'-end region of the template RNA, a technique based on the template switching method can be used in the preparing-decoding step, for example. The template switching method (nano-CAGE method) is not particularly limited, and, for example, Plessy et al., 2010 Nature Methods 7, 528-534 can be referenced.

When the nucleic acid to be prepared in the preparing-decoding step of the decoding method of the present invention includes an RNA nucleic acid of the 5'-end region of the template RNA or a complementary DNA nucleic acid corresponding to the 5'-end region of the template RNA, a technique based on the HeliScopeCAGE method can be used in the preparing-decoding step, for example. The HeliScopeCAGE method is not particularly limited, and, for example, Kanamori-Katayama et al., 2011 Genome Res. 21 (7): 1150-1159 can be referenced.

When the nucleic acid to be prepared in the preparing-decoding step of the decoding method of the present invention includes at least one nucleic acid of an RNA nucleic acid of the 5'-end region of the RNA or a complementary DNA nucleic acid corresponding to the 5'-end region of the RNA, a technique based on the CAGE method can be used in the preparing-decoding step, for example. The CAGE method is not limited to particular methods. As the CAGE method, for example, WO 2003/106672, JP 2005-535311 A, or JP 2009-72062 A can be used as reference.

The preparing-decoding step in the present embodiment based on the CAGE method includes: for example, a preparing step of preparing a linker-added nucleic acid having a linker bound to the nucleic acid; a cleaving step of cleaving the linker-added nucleic acid using a restriction enzyme having a recognition site in the linker and a cleavage site in the nucleic acid; and a collecting step of collecting a fragment corresponding to the 5'-end region of the RNA from the obtained cleavage product. When the nucleic acid is a DNA nucleic acid corresponding to the 5'-end region of the RNA, the linker-added nucleic acid is, for example, a linker-added DNA nucleic acid, a fragment corresponding to the 5'-end region of the RNA is a (complementary) DNA fragment corresponding to the 5' end of the RNA. When the nucleic acid is a complementary DNA nucleic acid corresponding to the 5'-end region of the RNA, the linker-added nucleic acid is, for example, a linker-added RNA nucleic acid, and the fragment corresponding to the 5' end of the RNA is a (complementary) RNA fragment corresponding to the 5' end of the RNA.

The preparation of the linker-added DNA nucleic acid in the preparing step is not limited to particular preparations, and can be, for example, the following preparations:
(1) A DNA nucleic acid to a template RNA is synthesized, and a linker is bound to the DNA nucleic acid to prepare the linker-added DNA nucleic acid;
(2) A 5'-end cap structure of a template RNA is substituted with oligonucleotide corresponding to a linker, and a DNA nucleic acid to the obtained 5'-end-substituted template RNA is synthesized to prepare the linker-added DNA nucleic acid.

The preparing step of the item (1) above includes, for example, the following steps (1a) and (1b):
(1a) the step of preparing a DNA nucleic acid to a nucleotide sequence of the 5' end of the template RNA; and
(1b) the step of binding at least one linker to the DNA nucleic acid.

The linker is a sequence having a recognition site of a restriction enzyme used in the cleaving step. For example, a cleavage site of the restriction enzyme is present in, for example, the DNA nucleic acid corresponding to the 5'-end region of the template RNA in the linker-added DNA nucleic acid having a linker bound thereto. Thus, the linker-added DNA nucleic acid is cleaved by the restriction enzyme in the cleaving step, and a DNA fragment corresponding to the 5'-end region of the template RNA is cleaved off.

The preparation of the DNA nucleic acid in the step (1a) can be performed by reverse transcription using a template RNA, for example and specifically performed by amplifying a DNA nucleic acid corresponding to the template RNA using DNA polymerase.

One kind of the DNA polymerase can be used alone or a cocktail of two or more kinds of DNA polymerase may be used. The DNA polymerase is preferably, for example, thermally stable, and specific examples thereof include Taq polymerase, Pwo DNA polymerase, Kod DNA polymerase, Pfu DNA polymerase, Vent DNA polymerase, Deep Vent DNA polymerase, rBST DNA polymerase, and Mater Amp Ampli Therm DNA polymerase.

In the amplification, various reagents required for the reverse transcription can be used and can be, for example, random primers.

For example, the step (1a) may include: the step of substituting the 5' cap structure of the template RNA with oligonucleotide; and the step of synthesizing a first cDNA strand using, as a template, the template RNA to prepare a DNA nucleic acid to a nucleotide sequence of the 5' end of the template RNA.

For example, the step (1a) may include: the step of synthesizing a first cDNA strand using, as a template, the template RNA to generate a cDNA-RNA hybrid; the step of selecting, from the cDNA-RNA hybrid, a specific cDNA-RNA hybrid having the 5' cap structure using a selective binding substance that specifically recognizes the 5' cap structure; and the step of collecting a DNA nucleic acid corresponding to the nucleotide sequence of the 5' end of the template RNA.

The selective binding substance is not limited to particular substances, and examples thereof include a cap-binding protein or a cap-binding antibody.

The selective binding substance may be in the state of being bound to a support, for example. The support is not limited to particular supports, and examples thereof include magnetic beads, agarose beads, latex beads, a sepharose matrix, a silica gel matrix, and glass beads.

For example, the step (1a) may include: the step of synthesizing a first cDNA strand using, as a template, the template RNA to generate a cDNA-RNA hybrid; and the step of collecting, from the cDNA-RNA hybrid, a DNA nucleic acid corresponding to a nucleotide sequence of the 5' end of the template RNA.

For example, the step (1a) may include: the step of synthesizing a first cDNA strand using, as a template, the template RNA to generate a cDNA-RNA hybrid; the step of causing a selective binding substance (first substance) to the 5' cap structure to conjugate with the cDNA-RNA hybrid; the step of causing the cDNA-RNA hybrid to be in contact with a support on which another matching selective binding substance (second substrate) has been immobilized; and the step of collecting, from the cDNA-RNA hybrid immobilized on the support, a DNA nucleic acid corresponding to a nucleotide sequence of the 5' end of the template RNA. The another matching selective binding substance (second substance) specifically binds to the selective binding substance (first substance), for example. Thus, by causing the cDNA-RNA hybrid to be in contact with the support, the selective binding substance (first substance) binding to the hybrid and the matching selective binding substance (second substance) immobilized on the support are bound to each other. Accordingly, the hybrid is immobilized on the support.

A combination of the selective binding substance (first substance) and the matching selective binding substance (second substance) is not limited to particular combinations. The combination may be, for example, a combination where the selective binding substance (first substance) is biotin, and the matching selective binding substance (second substance) is selected from the group consisting of derivatives of avidin, streptavidin, and biotin that specifically bind to avidin, streptavidin, and biotin. The combination may also be, for example, a combination where the selective binding substance (first substance) is digoxigenin, and the matching selective binding substance (second substance) is an antibody to digoxigenin. The support is, for example, the same as mentioned above.

For example, the step (1b) includes: the step of binding the linker to the end region of the DNA nucleic acid corresponding to the nucleotide sequence of the 5' end of the template RNA; the step of synthesizing a second cDNA strand using, as a template, a DNA nucleic acid having a linker bound thereto (hereinafter also referred to as the "first cDNA strand"); the step of treating, with a restriction enzyme, a double-stranded cDNA (hereinafter also referred to as the "linker-bound double-stranded cDNA") between the obtained first cDNA strand having a linker bound thereto and the obtained second cDNA strand; and the step of collecting, from a degradate obtained by the restriction enzyme, the linker and a part of cDNA corresponding to a nucleotide sequence of the 5' end of the template RNA. The linker preferably has, for example, at least one recognition site of the enzyme, and the restriction enzyme is preferably, for example, an enzyme that cleaves a site that is different from the recognition site. In the fragment, the linker may include, for example, a part of the linker or the entire sequence of the linker.

In the step (1b), the linker may include, for example, a double-stranded oligonucleotide region. In this case, the second cDNA strand may be synthesized using the linker, for example.

In the step (1b), the second cDNA strand may be synthesized using another oligonucleotide that partially or entirely corresponds to the linker, for example.

In the step (1b), the linker may be bound to a selective binding substance (first substance) or may include the selective binding substance (first substance) inside, for example. In this case, the step of collecting in the step (1b) includes, for example, the step of causing a degradate of the restriction enzyme to be in contact with a support on which another matching selective binding substance (second substance) has been immobilized to bind the selective binding substance (first substance) to the matching selective binding substance (second substance), thereby collecting the support. The fragment collected in the step (1b) includes the linker, as mentioned above. Thus, when the selective binding substance in the linker and the matching selective binding substance (second substance) immobilized on the support are bound to each other, the fragment is bound to the support, and the fragment can be collected by collecting the support. Examples of the selective binding substance (first substance), the matching selective binding substance (second substance), and the support are the same as those mentioned above.

In the step (1b), the restriction enzyme is not limited to particular enzymes, and examples thereof include a Class II restriction enzyme and a Class III restriction enzyme. Examples of the Class II restriction enzyme include a Class IIG restriction enzyme and a Class IIS restriction enzyme. The restriction enzyme can be specifically, for example, selected from the group consisting of GsuI, MmeI, BpmI, BsgI, EcoP15I, and XmaJI.

The preparing step of the item (2) above includes, for example, the following steps (2a), (2b), and (2c):
(2a) the step of substituting the 5' cap structure of the template RNA with oligonucleotide;
(2b) the step of synthesizing a first cDNA strand using, as a template, the template RNA; and
(2c) the step of synthesizing a second cDNA strand using, as a template, the first cDNA strand.

In the preparing step of the item (2) above, a double-stranded cDNA of the first cDNA strand and the second cDNA strand is obtained as a linker-added DNA nucleic acid by the steps (2b) and (2c). In the cleaving step, this double-stranded cDNA is subjected to a restriction enzyme treatment.

In the preparing step of the item (2) above, the oligonucleotide can also be referred to as the linker. The oligonucleotide has a sequence having a recognition site of a restriction enzyme to be used in the cleaving step inside. The first cDNA strand synthesized in the step (2b) has, on the 3' side thereof, a sequence (linker) corresponding to the oligonucleotide, and the second cDNA strand synthesized in the step (2c) has the same sequence (linker) as the oligonucleotide, and each of the first cDNA strand and the second cDNA strand has a cleavage site of the restriction enzyme in a DNA nucleic acid corresponding to the 5'-end region of the template RNA. Thus, in the cleaving step, the double-stranded cDNA (linker-added DNA nucleic acid) is cleaved by the restriction enzyme, and a DNA fragment corresponding to the 5'-end region of the template RNA is cleaved off.

In the decoding method of the present invention, the cleaving step following the preparation is, as mentioned above, a step of cleaving the linker-added DNA nucleic acid using a restriction enzyme having a recognition site in the linker and a cleavage site in the nucleic acid.

The restriction enzyme in the cleaving step is not limited to particular enzymes and can be determined, as appropriate, according to the linker. As the restriction enzyme, any of the examples mentioned above can be used, for example.

In the decoding method of the present invention, the step following the cleaving step is a step of collecting, from the obtained cleavage product, a DNA fragment corresponding to the 5'-end region of the RNA. The method for collecting the DNA fragment is not limited to particular methods.

The length of the DNA fragment to be collected is not limited to particular lengths and is, for example, 5 to 100 bp, 15 to 30 bp, 10 to 30 bp.

In the decoding method of the present invention, the collected DNA fragment may be linked with the vector, for example. Subsequently, the sequence of the DNA fragment may be determined using the vector to which the DNA fragment has been linked, for example.

In the decoding method of the present invention, at least two collected DNA fragments may be linked with each other to prepare a concatemer, and subsequently, the concatemer may be linked with a vector, for example.

(DNA Element Analysis Method)

The analysis method of the present invention is, as mentioned above, a method for analyzing a DNA element, including: a decoding step of decoding a base sequence of a nucleic acid corresponding to a 5' end region of an RNA by the decoding method of the present invention, and a mapping step of mapping of a DNA element that encodes synthesis of the RNA to a genome sequence on the basis of information on the decoded base sequence.

In the analysis method of the present invention, "analysis" includes the meanings of identification of the position of the DNA element in the genome and qualitative determination or quantitative determination of activity level of the DNA element, for example. In the analysis method of the present invention, "the number of overlapping portions (or the expression level) of the nucleic acid" can also be referred to as "the degree of activation" of the DNA element, for example. In the case where RNA is expressed by activation of the DNA element, the expression level of the RNA indirectly corresponds to the activity level of the DNA element, and the expression level of the nucleic acid (e.g., fragment such as a DNA fragment) prepared using, as a template, the RNA also indirectly corresponds to the activity level of the DNA element.

In the present invention, the "DNA element" that is an object to be analyzed may be, for example, known or unknown. The present invention can identify the position of the unknown DNA element in the genome and can determine the activity level of the unknown DNA element, for example.

The "DNA element" in the present invention is, as mentioned above, a "DNA element that encodes synthesis of the RNA", specifically a DNA element that encodes "synthesis of RNA by activation". For example, the enhancer does not generate RNA from the enhancer itself by activation but bidirectionally generates RNA from both ends and is a functional DNA element that encodes synthesis of the RNA caused by activation, as mentioned above. Thus, in the present invention, the DNA element that encodes synthesis of the RNA can also be referred to as a DNA element that encodes "synthesis of RNA corresponding to a region that is different from the DNA element in the genome" by activation. The present invention, however, is by no means limited thereto, and the DNA element may encode "synthesis of RNA corresponding to the DNA element itself", for example.

The analysis method of the present invention can identify the DNA element by the mapping step, for example. Moreover, the analysis method of the present invention can determine the activity level of the DNA element on the basis of the number of overlapping portions in the mapped DNA fragment, for example.

The following shows the decoding method and the analysis method of the present invention as examples. The present invention, however, is by no means limited thereto.

(Step 1)

The step 1 is to selectively collect cDNAs containing a site corresponding to the 5' end of RNAs in a sample. The cDNAs may be synthesized, for example, by using the RNAs as templates.

RNA collected from desired cells, tissues, or organisms can be used as a starting material. The method for preparing the RNA is, for example, as mentioned above.

Moreover, a full-length cDNA library may be used to isolate the 5' end nucleic acids corresponding to the 5' end of the transcribed part of a gene.

The step 1 itself can be performed by a publicly known method. In other words, methods to construct full-length cDNAs and methods to synthesize cDNA fragments at least containing a site corresponding to the 5' end of the RNAs are already known, and any of these methods can be adopted. One of the preferable methods is the cap trapper method (e.g. Piero Caminci et al., Methods in Enzymology, Vol. 303, pp. 19-44, 1999). This cap trapper method is described below. However, the present invention is not limited to the use of the cap trapper method, and other approaches to enrich or select cDNAs could be applied as well.

The cap trapper method first synthesizes the first-strand cDNA with a reverse transcriptase using RNA as a template. This can be performed by a known method. The cDNA can be primed with an oligo-dT primer or, when the template RNA is mRNA, it can be primed with a random primer. It is advisable to add trehalose to the reactive solution because it raises the efficiency of reverse transcription reaction by stabilizing the reverse transcriptase (U.S. Pat. No. 6,013,488). It is preferable to use 5-methyl-dCTP instead of standard dCTP, because it avoids internal cDNA cleaved with several restriction enzymes and prevents unintended cleavage with restriction enzymes to a considerable extent. In addition, after the first-strand cDNA synthesis, proteins and digested peptides might be removed by CTAB (cetyl trimethyl ammonium bromide) treatment, or other more general methods to purify cDNA.

Next, a selective binding substance is bound to the cap structure of RNA. A "selective binding substance" here means a substance that selectively binds to a specific substance. Such selective binding substance includes preferably biotin, but is not limited to biotin. The cap structure is generally a structure of the 5' end of mRNA and can also be found in an enhancer RNA that is a transcript of enhancer, thus allowing for a specific selection of enhancer RNA. Therefore, when RNA is used as the starting substrate, the selective binding substance only binds to the cap structure of RNA. In addition, the selective binding substance does not bind to RNA if the cap structure at the 5' end has been lost. Biotin can be bound to the cap structure by a known method. For example, the cap structure can be biotinylated by first oxidizing the diol group within the cap structure by treating RNA with an oxidizer such as $NaIO_4$ and making them react with biotin hydrazide.

Single-strand RNA is cleaved by means such as RNase I treatment. Any other RNase that can cleave single strand RNAs but not cDNA-RNA hybrids or cocktails of RNases that can cleave various single-strand RNA sequences with various specificities can be used alternatively. In an cDNA-RNA hybrid whose first-strand cDNA has been extended to the site corresponding to the 5' end of RNA, the vicinity of the 5' end of RNA is single-stranded due to its failure to be hybridized with cDNA. Thus, the hybrid is cleaved at the single-stranded part and loses its cap structure through this step. Consequently, this step leaves only those RNA-cDNA hybrids with cDNA that fully extends to the 5' end of RNA to maintain the cap structure.

A matching selective binding substance fixed to a support, which selectively binds to the aforementioned selective binding substance, is prepared. In the present specification, a "matching selective binding substance" means a substance that selectively binds to the aforementioned selective binding substance, which, in the case where the selective binding substance is, for example, biotin, would be avidin, streptavidin or a derivative thereof that binds specifically to biotin or its derivatives. The support can favorably be, but is not limited to be, magnetic beads, particularly magnetic porous glass beads. Since magnetic porous glass beads to which streptavidin has been fixed are commercially available, such commercial streptavidin coated magnetic porous glass beads can be used. Similarly other materials such as latex beads, latex magnetic beads, agarose beads, polystyrene beads, sepharose beads or alike could be used instead of porous glass beads. Furthermore, the present invention is not limited to the use the biotion-avidin system but other binding substances could be used like a digoxigenin tag that would be attached to the cap structure and digoxigenin recognizing antibodies attached to a solid matrix.

Following this, the aforementioned RNA-cDNA hybrid with the cap structure is made to react with the aforementioned matching selective binding substance fixed to the support in order to bind the selective binding substance on the cap structure with the matching selective binding substance on the support, thereby immobilizing the RNA-cDNA hybrid with the cap structure on the support. When magnetic beads are used as the support, applying a magnetic force can quickly collect the magnetic beads. Meanwhile, in order to prevent non-specific binding to the support, it is preferable to treat the support with a large excess of DNA-free tRNA for blocking such binding before performing this reaction. Other substances that are suitable for blocking the surface are, for example, nucleic acids or derivatives, for example total RNA or oligonucleotides; proteins, for example bovine serum albumin; polysaccharides, for example glycogen, dextran sulphate, heparin or other polysaccharides. Hybrid molecules containing parts of all of the above could be used to mask non-specific binding sites.

The above focuses on the case where the step 1 is performed by the cap trapper method, but other methods can also be used as long as, for example, they can selectively collect cDNAs containing a site complementary to the 5' end of RNA.

Alternatively to the cap-selection, one could dephosphorylate the 5' ends of RNAs with a phosphatase, such as BAP (bacterial alkaline phosphatase), followed by treatment with the decapping enzyme TAP (tobacco acid pyrophosphatase). Subsequently, a ribonucleotide or a deoxyribonucleotide can be attached to the 5' end of the RNA instead of the original cap-structure with RNA ligase (Maruyama K, Sugano S. Gene 138, 171-4 (1994)). In this way, for example, a Class II or Class III recognition site can be placed in the oligonucleotide or ribonucleotide sequence used during the ligation step, which is placed at the 5' end of a cDNA or RNA. This Class II or Class III restriction enzyme can then be used to cleave within the cDNA and produce the 5' end tag.

Alternatively to biotin, a cap-binding protein (Pelletier et al., Mol Cell Biol 1995 15:3363-71; Edery I. et al., Mol Cell Biol 1995 June; 15(6):3363-71) or an antibody (Theissen H et al., EMBO J. 1986 Dec. 1; 5(12):3209-17) that specifically binds to the cap structure can be used as the aforementioned selectively binding substance.

Alternatively, one could use methods to attach oligonucleotides chemically to the cap structure as described by Genset. This method is based on the oxidation of cap structure (U.S. Pat. No. 6,022,715). This allows (1) adding to the cap an oligonucleotide which may contain a recognition side for a Class IIS or Class III restriction enzyme, and (2) preparing first-strand cDNA which then switches second-strand cDNA synthesis.

Alternatively, one could use the cap-switch method as described by Clontech (U.S. Pat. No. 5,962,272). One could prepare the first-strand cDNA in the presence of a cap-switch oligonucleotide which carries a recognition site for a substance capable of recognizing nucleic acids and cleaving them apart from the recognition sequence, so that Class IIS or Class III restriction enzyme may be used. The cap switch mechanism lets the first strand synthesis continue on the cap-switch oligonucleotides. This can be continued by a second-strand cDNA synthesis, or followed by a PCR step as described for example in the SMART™ Clontech cloning system.

In another embodiment, depending on the quality of RNA, random priming and extending the cDNA up to the cap-structure may allow for the utilization of 5' ends. Particular enzyme and reaction conditions allow sometimes reaching the cap-site with high efficiency (Carninci et al, Bio techniques, 2002). Even without a cap-selection, it is possible to attach, in place of the cap structure, oligonucleotides that carry Class IIS or Class III restriction enzyme sites that would be later used to produce concatemer.

Finally, the cDNA can be cleaved with the Class II (Class IIS or Class IIG) or Class III restriction enzyme to produce 5' end tags. The 5' end tags are used in the subsequent formation of concatemer. Any other methods, including mechanical cleavage, may possibly be used.

Figure 1:
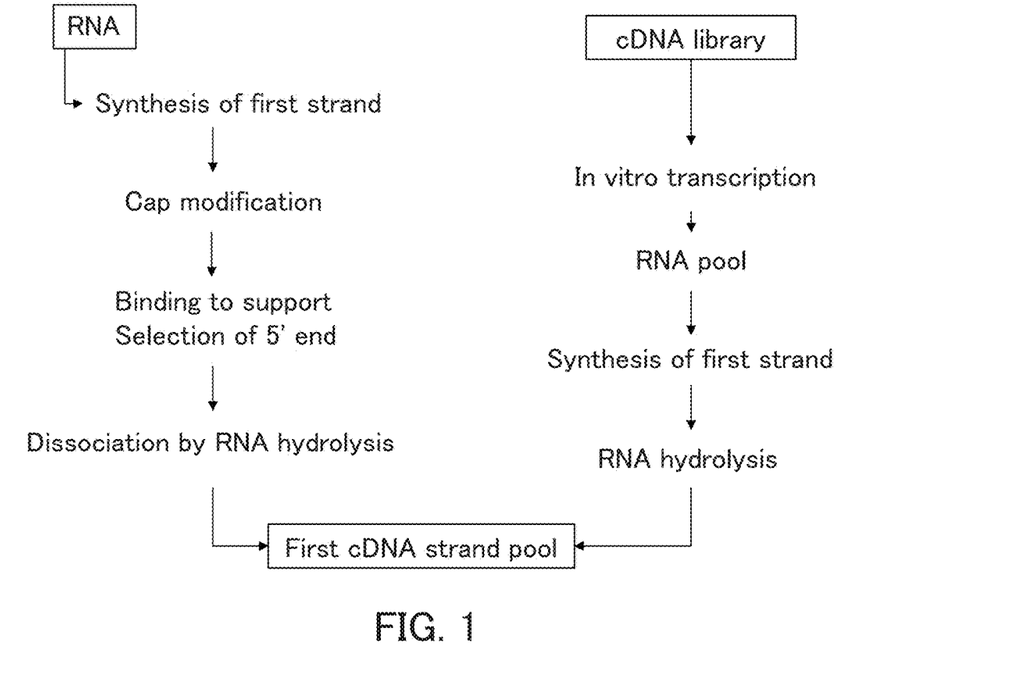
FIG. 1 is a schematic view showing exemplary steps of the present invention

FIG. 1 summarizes exemplary workflows according to the present invention. According to FIG. 1, to perform the method of the present invention, 5' ends of transcribed regions can be isolated from a plurality of RNA molecules or, a plurality of RNA molecules that have been enriched for RNA fractions from enhancers, or a full-length cDNA library.

When applying the present method to a plurality of RNA molecules, RNA molecules may be used as templates to synthesize complementary cDNA strands. The cDNA strands proceed to a selection step so as to enrich RNAcDNA hydrides including the 5' ends of the transcribed regions. After the removal or destruction of the mRNA portion by hydrolysis with an alkali, a first-strand cDNA pool including the 5' ends of the transcribed regions is prepared.

In a different embodiment of the present invention, a full-length cDNA library can be used to prepare a RNA pool including the 5' ends of the cDNA clones. A single-stranded cDNA pool is then synthesized using the aforementioned RNA pool as a template. A first-strand cDNA portion thereof is obtained after the removal or destruction of the RNA molecules by hydrolysis with an alkali, and the resulting first-strand cDNA pool includes the 5' ends of the transcribed regions. The transcribed regions are available for further processing under the present invention. Note that when starting from a full-length cDNA library, no selection for 5' ends is required.

(Step 2)

In continuation of the step 1, the following step 2 is carried out to selectively collect fragments containing a cDNA site that at least contains a site complementary to the 5' end of RNA.

When using the aforementioned cap trapper method, the first-strand cDNA that has been immobilized on the support is released. It can be performed by treating the support with alkali, such as sodium hydroxide. Alternatively to alkali, an enzymatic reaction with RNaseH (which cleaves only the RNA hybridized to DNA) could be used. The alkali treatment releases the cDNA from the RNA-cDNA hybrid, bound to the support through the cap on the RNA, and separates the cDNA from the RNA to only leave first-strand cDNA on its own.

Then, a linker is added to the cDNA that holds a sequence recognized in a sequence-specific manner by a substance having an enzymatic activity that cleaves the recognized DNA outside the recognition sequence. Such substances include but are not limited to certain Class II and Class III restriction enzymes.

In this embodiment, a linker that at least carries a Class IIS or Class III restriction enzyme site and a random oligomer part at the 3' end are ligated to the end of this first-strand cDNA, which corresponds to the 5' end of the aforementioned RNA (i.e., the 3' end of the cDNA). For the later cloning of the 5' end sequence tags into concatemers, it is preferable, but not essential, to introduce a second recognition site into the linker. The second recognition site is preferably distinct from the aforementioned recognition site used for, for example, the Class IIS or Class III restriction enzyme.

This can preferably be performed using a linker that carries a Class IIS or Class III restriction enzyme site and a random oligomer part (SSLLM (single strand linker ligation method), Y. Shibata et al., BioTechniques, Vol. 30, No. 6, pp. 1250-1254, (2001)). The Class IIS and Class III restriction enzymes are restriction enzyme groups that cause cleavage at parts other than the recognition site. An example for a Class IIS restriction enzyme includes, but is not limited to, the use of GsuI. GsuI treatment cleaves one of the strands at 16 bp downstream from the recognition site, and the other strand at 14 bp downstream from the recognition site.

Another suitable example is MmeI, which cleaves respectively 20 and 18 bases apart from its recognition sequence. An example for a Class III restriction enzyme includes, but is not limited to, EcoP15I, which cleaves respectively 25 and 27 bp apart from its recognition site. The random oligomer part is located at the 3' end of the linker, and though the number of bases is not particularly restricted, the recommended number is 5 to 9, or more preferably, 5 to 6. The Class IIS or Class III restriction enzyme site is preferably located close to the aforementioned random oligomer part, so that the cleavage point comes within the cDNA. The linker is preferably a linker of double-stranded DNA of which the aforementioned random oligomer part protrudes to the 3' end and provides the binding end. In addition, it is advisable to bind a selective binding substance such as biotin to the linker in advance to facilitate its collection later.

When the aforementioned first-strand cDNA is made to react with such a linker, the random oligomer part of the linker hybridizes with the 3' end of the first-strand cDNA (i.e. the 5' end of the template RNA). Next, the second-strand cDNA is synthesized by using this linker as a primer and the first-strand cDNA as a template. This step can be performed by a standard method. In a different embodiment of the present invention, the first-strand cDNA can be removed by hybridization against a plurality nucleic acids followed by physical separation of single-stranded and double-stranded DNA-DNA or double-stranded DNA-RNA hybrids. Such a removal step can be performed by, but is not limited to, the method disclosed in US patent publication No. 20020106666. Single-stranded cDNA collected in the removal step is used as a template for second strand synthesis by standard procedures similar to the aforementioned approach omitting a removal step.

Then, the obtained double-strand cDNA is treated with the above Class IIS or Class III restriction enzyme. In this step, a double-strand cDNA fragment including a linker-derived part and a part derived from the 5' end of the cDNA (the 5' end of the second-strand cDNA) is prepared. For example, if GsuI is to be used as the Class IIS restriction enzyme and if a linker is designed to locate the restriction site immediately upstream from the aforementioned random oligomer site, the obtained DNA fragment would include a site derived from the site on the 5' end of the second-strand DNA (i.e. the site on the 5' end of the RNA) of the length of 16 bp (the complementary strand is 14 bp). In the case of using MmeI, the length of the second-strand DNA fragment should increase to 20 and 18 bp, respectively, and in the case of EcoP15I, to 25 and 27 bp, respectively.

Next, such DNA fragments are selectively collected. If a selective binding substance (e.g. biotin) had been bound to the linker as above, the collection could be performed similarly to the step 1 by using a support to which a matching selective binding substance (e.g. streptavidin) would be fixed. This procedure completes the step 2, which selectively collects fragments containing a cDNA site, belonging to the first-strand cDNA, which at least contains a site complementary to the 5' end of the aforementioned RNA.

The above explains the case where the SSLLM is used for the step 2, but the step 2 can also be carried out by any other method as long as the method can selectively collect fragments containing the 3' end of the first-strand cDNA (the 5' end of the template mRNA). For example, it is possible to use exonuclease that cleaves the nucleotide in the 5' to 3' direction at a controlled speed. The exonuclease treatment of the first-strand cDNA for a prescribed time period leaves a single-strand fragment including the 3' end of the first-strand cDNA (the 5' end of the template RNA). It is possible to obtain only the targeted single-strand fragments by performing treatment with a nuclease that only splits double-strand fragments. These fragments can be collected, linked with adapters and cloned.

The above selected fragments that correspond to the 5' end can be further ligated to linkers and then used for PCR amplification in case that the quantity is insufficient for the downstream applications such as cloning.

In one embodiment, the fragments corresponding to the 5' part of RNAs are ligated on the 3' end to a linker carrying just another restriction enzyme site, which may be distinct from the restriction site used in the first linker. Thereafter, the fragments corresponding to the 5' end of mRNA contain linkers carry recognition sites for restriction enzymes at both sides. Such fragments can be amplified by PCR followed by subsequent cleavage by one or two restriction enzymes to produce DNA fragments suitable for the cloning of concatemers as described below in more detail.

In another embodiment similar to a paper (Velculescu et al., 1995), the aforementioned DNA fragment or PCR product is initially used for forming dimmeric molecules included of two 5' end specific fragments ligated to one another in opposite orientation. These dimmers can then be used directly or after just another PCR amplification to produce concatemers as specified in more detail below.

In just another embodiment of the present invention, alternatively to PCR-amplified DNA, RNA polymerase could primarily amplify fragments corresponding to 5' ends having appropriate linkers at both ends. DNA fragments are then reconstituted by a reverse transcription step and a second strand formation to allow for concatemer formation.

(Step 3)

The subsequent step 3 forms concatemers by mutually ligating the collected fragments. Since there are multiple RNAs and the linker hybridizes with the first-strand cDNA at the random oligomer part as above, the above method can obtain fragments containing multiple cDNAs derived from multiple RNAs within a sample. The step 3 ligates these multiple fragments and forms concatemers. The ligation of the cDNA fragments can be carried out by a standard method, using commercial ligation kits based on but not limited to T4 DNA ligase. The ligation can be securely performed but is not limited to a method, which first is introducing a second linker providing a recognition site for a restriction enzyme that is distinct from the other recognition sites used at the earlier stages, which is then ligating two fragments into dimmers including two 5' tags in the opposite direction (di-tag), and which is further ligating such ligated di-tag fragments into concatemers. However, the performance of the present invention is not dependent on the cloning of intermediary di-tags. Monomeric tags can be self-ligated directly to form concatemers of satisfied length to perform the present invention. Thus, the present invention is neither limited to nor dependent on the use of di-tags. The number of ligated fragments is not restricted, practically any number of two or more, and preferably at least 20 to 30 is suitable to perform the present invention. The obtained concatemers are preferably but not limited to be amplified or cloned by a standard method.

The concatemers obtained in this way each include a site having the same base sequence (however, uracil in RNA would be thymine in DNA) as that of the 5' end of the multiple RNAs within the sample. Although it also includes a part derived from the linker or linkers, the base sequence of the linker or linkers is known from the experimental design, so the part derived from the linker or linkers and the part derived from RNA can be clearly distinguished by investigating the base sequence of the concatemer. Therefore, by determining the base sequence of the obtained concatemer, it is possible to find out the base sequences at the 5' end of multiple RNAs within the sample. The base sequences of a maximum of 16, 20 or 25 bases at the 5' end of each RNA can be learned by the preferable mode of using GsuI, MmeI or EcoP15I. Information on 16, 20 or 25 bases would be sufficient for almost definitely identifying the RNA statistically and to judge whether or not it is a new RNA. In addition, by determining the base sequence of the concatemer, it is possible to learn the base sequences at the 5' end of RNAs for the number of above fragments included in the concatemer (preferably 20 to 30), so information on the 5' end of multiple RNAs can be determined efficiently. The analysis of the concatemers can be automated by the use of computer software to distinguish between sequences derived from the 5' ends and sequences derived from a linker or the linkers.

Sequences from specific 5' end tags obtained from concatemers in the aforementioned form can be analyzed for their identity by standard software solutions to perform sequence alignments like NCBI BLAST (www.ncbi.nlm.nih.gov), FASTA, available in the Genetics Computer Group (GCG) package from Accelrys Inc. (www.accelrys.com), or the like. Such software solutions allow for an alignment of the 5' end specific sequence tags among one another to identify unique or non-redundant tags for clustering and further use in database searches. All such non-redundant sequence tags can then be individually counted and further analyzed for the contribution of each non-redundant tag to the total number of all tags obtained from the same sample. The contribution of an individual tag to the total number of all tags should allow for a quantification of the transcripts within a plurality of RNAs or a cDNA library. The results obtained in such a way on individual samples can be further compared with similar data obtained from other samples to compare their expression patterns against each other. Thus the present invention allows for the expression profiling of individual transcripts within one or more samples and the establishment of a reference database.

Specific 5' end sequence tags obtained as described above can further be used to identify transcribed regions within genomes for which partial or entire sequences were obtained. Such a search can be performed using standard software solutions like NCBI BLAST (www.ncbi.nlm.nih.gov) to align the 5' end specific sequence tags to genomic sequences. Though 20 bp tags were found to map specifically to genomic sequences, in some cases, it may be necessary to extend the initial sequence information obtained from concatemers for example by one of the approaches described below. The use of extended sequences allows for a more precise identification of actively transcribed regions in the genome. Similarly, the same approach and software solutions can be used to search for related sequences in other databases e.g. like NCBI (www.ncbi.nlm.nih.gov), EMBL-EBI (www.ebi.ac.uk), or DNA Data Bank of Japan (www.ddbj.nig.ac.jp).

Specific 5' end sequence tags which could be mapped to genomic sequences allow for the identification of regulatory sequences (Suzuki Y et al., EMBO Rep. 2001 May; 2(5): 388-93 and Suzuki Y et al., Genome Res. 2001 May; 11(5): 677-84). In a gene, the DNA upstream of the 5' end of transcribed regions usually encompasses most of the regulatory elements that are used in the control of gene expression. These regulatory sequences can be further analyzed for their functionality by searches in databases which hold information on binding sites for transcription factors. Publicly available databases on transcription factor binding sites and for promoter analysis including Transcription Regulatory Region Database (TRRD) (wwwmgs.bionet.nsc.ru), TRANSFAC (transfac.gbf.de), TFSEARCH (www.cbrc.jp), and Promoterinspector provided by Genomatix Software (www.genomatix) provide resources for computational analysis of promoter regions and enhancer regions.

Sequence information obtained from 5' end specific sequence tags or obtained by mapping a 5' end sequences to the genome can be further used to manipulate the regulation of a given target gene. In such an experiment, promoter related information would be used to alter its activity or to replace it with an artificial promoter. Alternatively, 5' end specific tags could provide sequence information for the design of anti-sense or RNAi probes for gene inactivation.

In a different embodiment of the present invention, sequence information derived from the concatemers can be used to synthesize specific primers for the cloning of full-length cDNAs. In such an approach, the sequence derived from a given 5' end specific tag is used to design a forward primer while the choice of the reverse primer would be dependent on the template DNA used in the amplification reaction. Amplification by the polymerase chain reaction (PCR) can be performed using a template derived from a plurality of RNAs obtained from a biological sample and an oligo-dT primer. In the first step the oligo-dT primer and a reverse transcriptase are used to synthesize a cDNA pool. In the second step, a forward primer derived from a 5' end specific tag and an oligo-dT primer are used to amplify a full-length cDNA from the cDNA pool. Similarly, a specific full-length cDNA can be amplified from an existing cDNA library using a forward primer derived from a 5' end tag and a vector nested reversed primer.

While the above method had used RNA within the sample as the starting substrate, the step 1 can be omitted by using an existing full-length cDNA library. In this way, information on the base sequences of the 5' end of multiple cDNAs (i.e. the 5' end of the RNAs used as templates for said cDNAs) contained in the full-length cDNA library can be efficiently obtained similarly to the above procedure.

Independent from the starting material used to perform the present invention, the single-stranded first-strand cDNA material can be fractionated by means of subtractive hybridizations and physical separation to allow for enrichment of the 5' ends of differentially expressed genes or for the concentration of transcripts of low abundance.

In some embodiments it could be desirable to obtain extended sequence information from the 5' ends of transcribed regions. Such extended sequences may allow in specific cases for the identification of start sites of protein synthesis or a better mapping to genomic sequences. As described above, the present invention included, in the step 2, the ligation of a linker to the 5' end of a cDNA. Introducing a single-stranded overhang encompassing a sequence obtained from a concatemer to bind to and to be ligated to a specific nucleic acid fragment allow such a linker to be used in a target specific manner. After the ligation, the linker can be used to enrich the DNA fragment by attaching the linker to a support from which it could be released after the enrichment. The linker can further be used as a primer to obtain extended sequence information on 5' ends in a liquid phase or on the solid phase used before enrichment.

By investigating the base sequences of the concatemers or extended 5' sequences obtained by the present invention, it is not only possible to clone new genes as described above, but also possible to investigate the expression profiles of genes within the sample. Furthermore, the technology can be used for various purposes such as to map transcription start sites in the genome, to map promoter usage patterns or enhancer usage patterns, for the analysis of SNPs in promoter regions or enhancer regions, for creating gene networks by combining the expression analysis with information on promoters and enhancers, alternative promoter usage or enhancer usage and on availability of transcription factors, and for selective collection of the promoter site or the enhancer site within fragmented genomic DNA. To select genomic fragments containing promoter sites, a fragment containing the same base sequence as the 5' end of mRNA could be bound to a support e.g. by using the aforementioned biotin system, and hybridized to fragmented genomic DNA. Hybridized genomic DNA fragments could then be separated from a mixture of genomic fragments by using e.g. streptavidin coated magnetic beads, and cloned under standard conditions.

Alternatively, concatemer cloning could be avoided by making and using selected 5' end tags ligated to a mixture of full-length cDNAs and bound to magnetic beads carrying homogeneous sequence of oligonucleotides, followed by ligation such as in the SSLLM, second-strand cDNA preparation and cleavage with a Class IIS or Class III restriction enzyme. The 5' end specific tag would be anchored specifically to the beads and would be used for the specific sequencing similarly as done by Lynx Therapeutics (U.S. Pat. Nos. 6,352,828; 6,306,597; 6,280,935; 6,265,163; and 5,695,934).

For example, oligonucleotides would have a "random part I", which will bind to 5' ends of cDNAs; and a code part of the oligonucleotide, which will be able to "tag" the ligation product. The oligonucleotide may be destroyed by exonuclease VII if not hybridized with a cDNA. The "decoder" oligonucleotides would be used to select out the sequence. The specific arrays of cDNAs on beads are then arrayed onto a solid surface, one per position, followed by parallel sequencing. The aforementioned approach would allow for the design of a liquid array format, in which each bead could be addressed by an independent label and processed individually for sequence analysis or alike.

In a different embodiment of the present invention, known 5' end specific tags can be used for an alternative analysis of 5' end specific sequences omitting the cloning and sequencing of concatemers. In such a case 5' end specific oligonucleotides of about 25 bp would be synthesized and fixed to a solid support to form a 5' end specific micro array. The hybridization of 5' tags obtained from a sample would then allow for the identification and quantification transcripts present in the sample. Standard methods for the preparation and use of microarrays are known to a person skilled in the art of molecular biology (Jordan B., DNA Microarrays: Gene Expression Applications, Springer-Verlag, Berlin Heidelberg N.Y., 2001: Schena A, DNA Microarrays, A Practical Approach, Oxford University Press, Oxford 1999).

By modifications as the aforementioned approaches for direct sequencing of 5' ends or a readout by hybridization to a 5' end specific microarray, the present invention provides different means for the general analysis of the 5' ends in the form of concatemers or the analysis of individual 5' ends, which were enriched by means of a 5' end specific selection.

Figure 2:
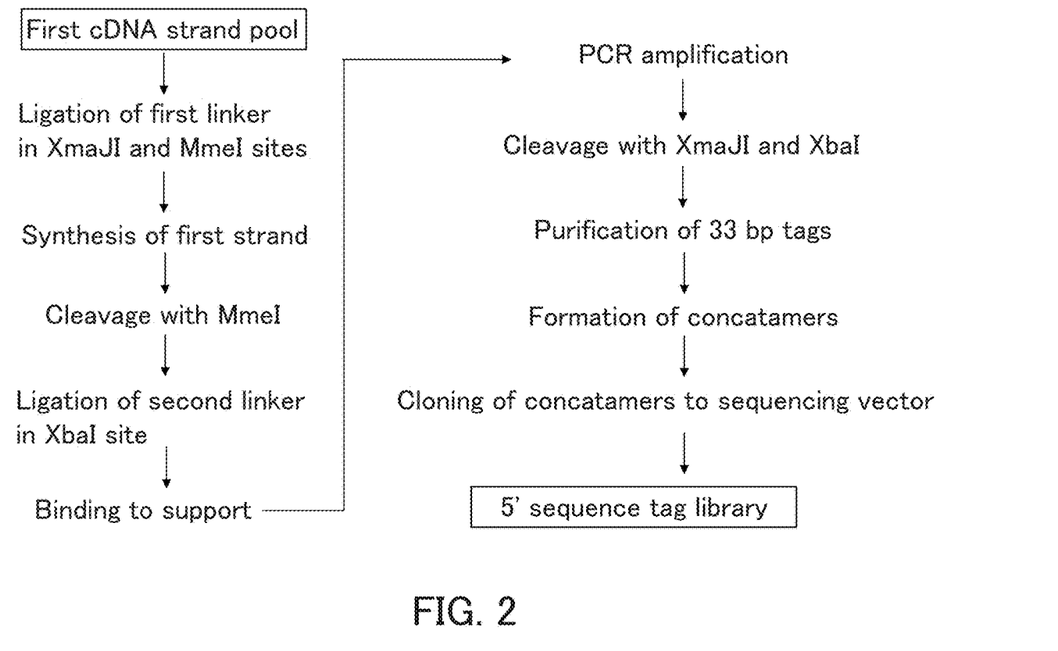
FIG. 2 is a schematic view showing exemplary steps of cloning 5' end specific tags to concatemer.

FIG. 2 summarizes the exemplary work flow according to the steps 2 and 3 discussed above. In FIG. 2, for example, the restriction enzymes XmaJI, MmeI and XbaI are used for the cloning of 33 bp DNA fragments. In principle, the cloning of 5' end specific tags includes the following steps.

In the initial step of the present invention outlined in FIG. 1, a pool of single-stranded cDNA is obtained. The pool includes the 5' end regions transcribed from the RNAs. Adjacent to the portion of the single-stranded cDNA which contains the 5' end regions transcribed from the RNAs, a specific linker, here denoted as the "first linker", is ligated to provide a recognition site for a restriction enzyme that cleaves outside the first linker with respect to its binding site or within the 5' end transcribed region. For the purpose of the example described in the figure, the restriction enzyme MmeI is used as it cleaves 21 bp downstream of the recognition site, thus allowing for the termination of tags which include the 5' ends of transcribed regions of RNAs. Also, a second restriction enzyme is given for the "first linker." For the purpose of this example, XmaJI is used for the later cloning of the 5' end specific tags.

Subsequently, the "first linker" is used to prime the synthesis of a second complementary cDNA strand, resulting in double-stranded cDNA molecules which include the 5' ends of transcribed regions of the RNAs and which have a recognition site for restriction enzymes that cleave at a site located outside the first linker with respect to its binding site adjacent to the region containing the 5' end regions transcribed the RNAs.

The aforementioned restriction enzyme that cleaves the outside of the binding site is, for the purpose of this example, MmeI. Cleavage with MmeI results in double-stranded cDNA fragments of the tags that include the 5' ends of transcribed regions of the RNAs and the "first linker" and that have a single strand DNA overhang at the cleavage site of MmeI.

To the aforementioned single-stranded DNA overhang at the cleavage site of MmeI, the "second linker" is ligated to provide a recognition site for a restriction enzyme suitable for the cloning of the cDNA fragments or tags that function as templates for amplification by means of PCR.

The cDNA fragment including the "first linker", cDNA fragments including the 5' ends of regions transcribed from the RNAs, and the "second linker" is purified by selective binding to a support by the means of a selective binding substance attached to the first linker.

For the purpose of the cloning of the cDNA fragments including the 5' ends of transcribed regions or tags, the aforementioned cDNA fraction including the "first linker", cDNA fragments or tags which include the 5' end regions transcribed from RNA, and the "second linker" are amplified by means of PCR, and the linker portions are cleaved off by restriction enzymes to allow for the ligation of the tags into concatemers. For the purpose of this example, the restriction enzymes XmaJI and XbaI are used, which cleave out a 33 bp fragment from the aforementioned cDNA fragments. After an appropriate purification step, the 33 bp fragments are ligated to each other for the formation of concatemers including, for example, up to 30 tags including the 5' ends of transcribed regions said RNA or cloned individually.

The concatemers can be cloned into a sequencing vector to prepare a library including the 5' end regions transcribed from RNA.

Figure 3:
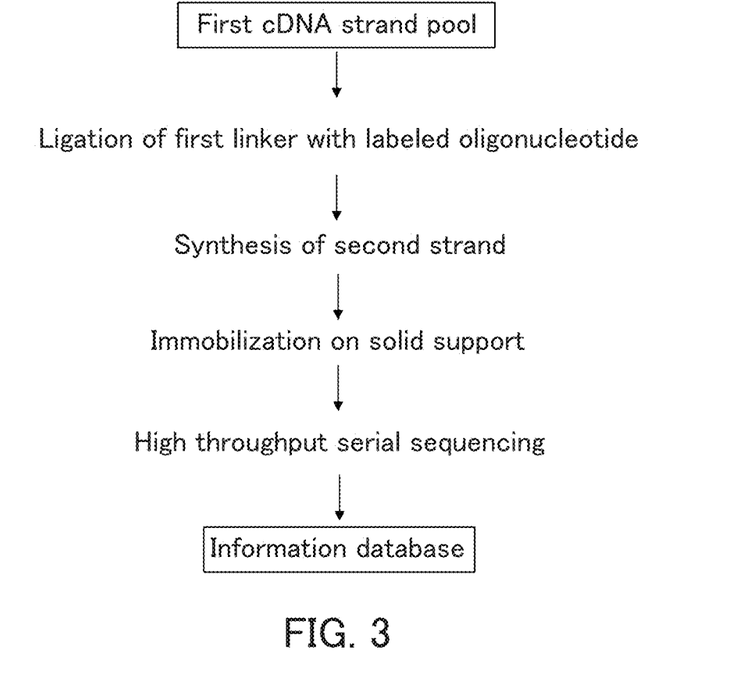
FIG. 3 is a schematic view showing exemplary steps of direct sequencing of 5' end tags.

FIG. 3 shows a principle workflow according to the present invention to illustrate an alternative approach for the direct sequencing of 5' end tags. For the purpose of this embodiment of the present invention, the single-stranded cDNAs which includes the 5' end regions transcribed from the RNAs and obtained as summarized in FIG. 1 are ligated to a linker, here denoted as "first linker", which for the purpose of this example, has a specific label to allow for the immobilization of the ligation product on a solid support. This linker can be used as a primer for the synthesis of a second strand cDNA complementary to the first strand. The single-stranded DNAs having a double-stranded linker adjacent to the region including the 5' end regions transcribed from the RNAs or double-stranded DNA including the 5' end transcribed regions can be forwarded for individual or parallel sequencing, for the purpose of this example, by a high throughput serial sequencing approach for the 5' ends of RNAs.

EXAMPLES

Example 1

Figure 4:
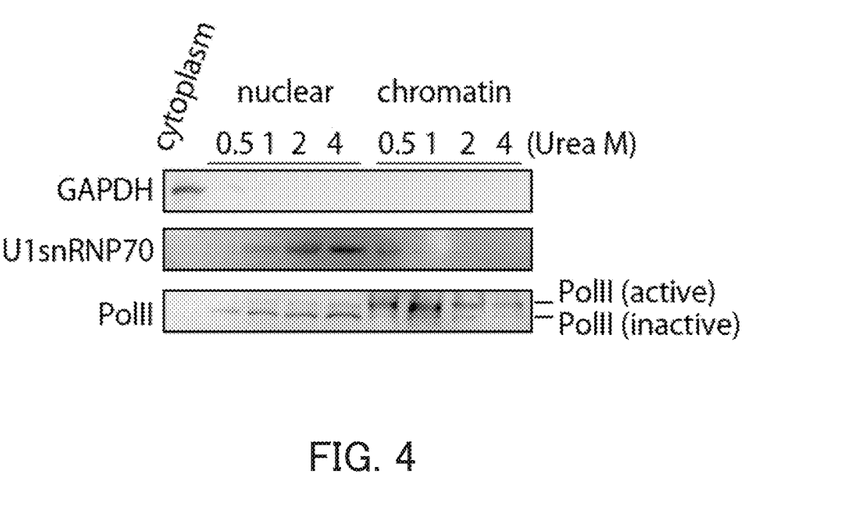
FIG. 4 shows the results of the Western blotting in Example 1.

First, nuclei were collected from MCF7 cells in the usual manner. To the collected nuclei, a denaturation buffer solution containing urea at a predetermined concentration (0.5, 1, 2, or 4 mol/L) was added to denature the nuclei with the urea. Then, nuclear components were separated into a soluble fraction (nuclear) and a chromatin fraction (chromatin). Thereafter, GAPDH, U1snRNP70, and polymerase II in the soluble fraction and the chromatin fraction were detected by Western blotting. GAPDH is a marker for cytoplasm, and U1snRNP70 is a marker for an intranuclear soluble fraction. The results of the Western blotting are shown in FIG. 4. As can be seen in FIG. 4, in relative terms, U1snRNP70 was detected in the soluble fraction and not detected in the chromatin fraction. This demonstrates that efficient fractionation was achieved successfully. In the chromatin fraction, phosphorylated active RNA polymerase (active Pol II) was concentrated, which indicates that RNA polymerase in the process of being synthesized was present in the chromatin fraction.

Example 2

A conventional CAGE method uses total RNA as a template RNA. Hereinafter, this method is referred to as an ordinary CAGE method. On the other hand, when the present invention is applied to a CAGE method, nascent RNA is used as a template RNA. Hereinafter, the CAGE method that uses nascent RNA as a template RNA according to the present invention is referred to as NET-CAGE (Native Elongating Transcript-Cap Analysis of Gene Expression) method of the present invention. In the present example, nascent RNA was obtained by collecting RNA from the chromatin fraction obtained in Example 1, and the NET-CAGE method was performed using the thus-obtained nascent RNA as a template. Then, the NET-CAGE method was compared with the ordinary CAGE method, which uses total RNA collected from MCF7 cells. Unless otherwise stated, the same applies to examples to be described below.

Figure 5:
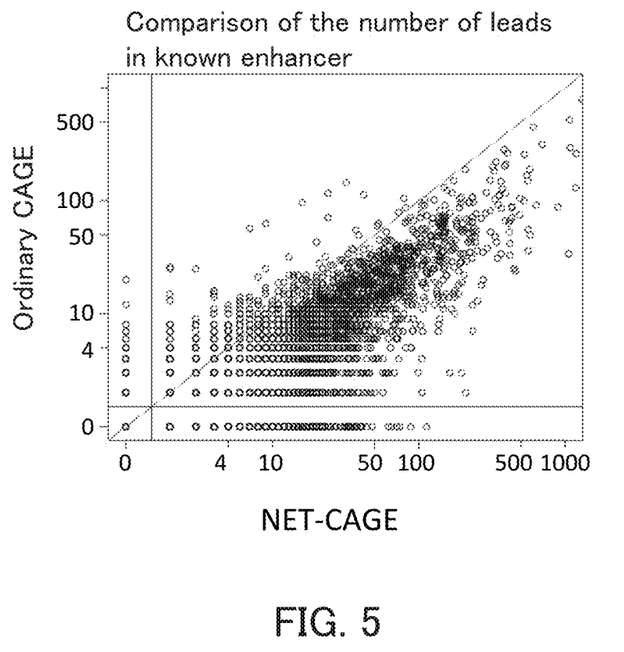
FIG. 5 is a graph showing the number of reads in Example 2.

Regarding known enhancer regions that were identified in the FANTOM 5 project and already reported in a paper (Andersson et al. Nature 2014), the number of reads in MCF7 cells obtained by the ordinary CAGE and the number of reads in MCF7 cells obtained by the NET-CAGE of the present invention are shown in the graph of FIG. 5. In FIG. 5, the X axis indicates the number of reads obtained by the ordinary CAGE, the Y axis indicates the number of reads obtained by the NET-CAGE, and each dot means one enhancer region. As can be seen in FIG. 5, in most of the enhancer regions, signals (the number of reads) obtained by the NET-CAGE of the present invention were at least from several times to ten times as great as those obtained by the ordinary CAGE. Further, while some enhancers were totally undetectable by the ordinary CAGE, many of them were detected by the NET-CAGE with a sufficient number of reads. From these results, it can be said that the NET-CAGE of the present invention can detect enhancers with a dramatically higher sensitivity as compared with the ordinary CAGE.

Example 3

Figure 6:
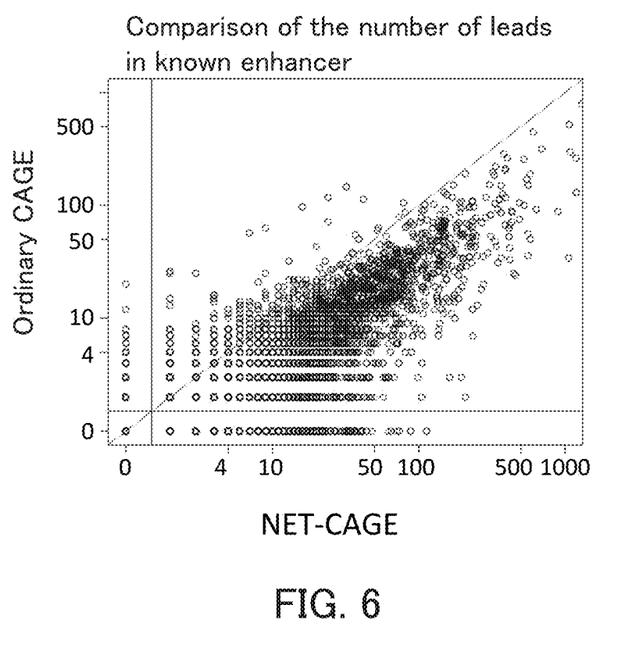
FIG. 6 is a graph showing repeatability of the number of reads in Example 3.

Regarding the known enhancer regions that were identified in the FANTOM 5 project and already reported in the paper (Andersson et al. Nature 2014), the repeatability was examined on the basis of the number of reads in MCF7 cells determined by the ordinary CAGE and the number of reads in MCF7 cells determined by the NET-CAGE of the present invention. The results obtained are shown in the graph of FIG. 6. In FIG. 6, the X axis and the Y axis indicate the number of reads mapped to the known enhancer regions identified in the paper. As can be seen in FIG. 6, when the ordinary CAGE was used, the correlation coefficient with respect to the number of reads shown in the paper was 0.69, and when the NET-CAGE of the present invention was used, the correlation coefficient with respect to the number of reads shown in the paper was 0.65. These results demonstrate that, similarly to the ordinary CAGE, the NET-CAGE of the present invention also can identify enhancers quantitatively with high repeatability and high reliability.

Example 4

Figure 7:
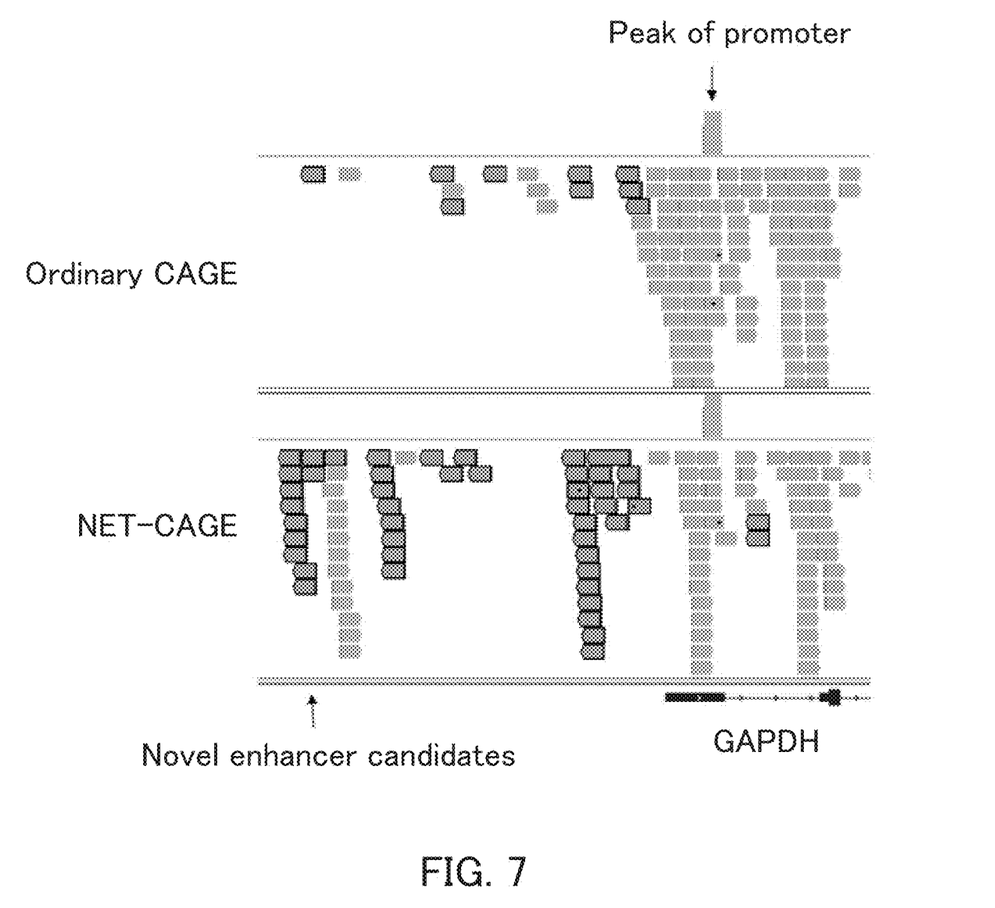
FIG. 7 is a view showing mapping of enhancer candidates in Example 4.

The ordinary CAGE and the NET-CAGE were performed using MCF7 cells. CAGE tag distributions in an upstream region of the GAPDH gene obtained by the ordinary CAGE and the NET-CAGE are shown separately in FIG. 7. FIG. 7 shows browser views of the genome browser of Integrative Genomics Viewer (IGV). In FIG. 7, mapped CAGE tags are shown at the genome coordinate positions shown therein, and the horizontal axis indicates the position coordinate of the genome. The purpose of the present example is to examine whether the NET-CAGE of the present invention can identify novel enhancer candidates that cannot be identified by the ordinary CAGE. To this end, FIG. 7 shows parts extracted from the browser views. Specifically, FIG. 7 shows tags present at the foot of the peak of a promoter shown in an upper part of FIG. 7. In FIG. 7, arrows not surrounded by frame lines indicate CAGE tags mapped in the sense direction, and arrows surrounded by frame lines indicate CAGE tags mapped in the antisense direction. The region indicated with a thin arrow is a region where the CAGE tags are distributed symmetrically in opposite directions. While the CAGE tags in this region were substantially undetectable by the ordinary CAGE, a sufficient number of CAGE tags were detected only by the NET-CAGE. As described above, a region where CAGE tags are present symmetrically in opposite directions is a distinctive characteristic observed in an enhancer, and this characteristic strongly suggests that this region is an enhancer. This region could not be identified as an enhancer in the FANTOM 5 project. Accordingly, this region can be regarded as a novel enhancer candidate identified by the NET-CAGE of the present invention. That is, it can be said that the NET-CAGE according to the present invention can identify novel enhancers undetectable by the ordinary CAGE.

The present invention will now be described by way of examples thereof. It should be noted that the present invention is not restricted to the Examples. The experiments described in the Examples can be performed by any person skilled in the art of standard techniques in the field of Molecular Biology. Unless otherwise defined in the text, the technical terms, abbreviations, and solutions used in the Examples should have the same meaning as commonly understood by a person skilled in the art in the field of the present invention. A general description of such terms, abbreviations and solutions can be found in the common reagent section in Molecular Cloning (Sambrook and Russel, 2001). All publications mentioned herein are incorporated into this document by reference to be disclosed and to describe the methods and/or materials therein.

The present application is based upon and claims the benefit of priority from Japanese patent application No. 2016-013575, filed on Jan. 27, 2016, and the entire disclosure of which is incorporated herein its entirety by reference.

INDUSTRIAL APPLICABILITY

As described above, the present invention can identify a functional DNA element such as an enhancer with higher sensitivity and can determine the transcription amount of the functional DNA element.

The invention claimed is:

1. A method for decoding a base sequence of a nucleic acid corresponding to a 5'-end region of an RNA, comprising:
    preparing a first nucleic acid from a template RNA that is an unlabeled nascent RNA,
    the first nucleic acid comprising (1) an RNA nucleic acid of a 5'-end region of the template RNA, or (2) a complementary DNA nucleic acid corresponding to the 5'-end region of the template RNA, or (3) a nucleic acid having a sequence that has two or more linked sequences of (1) the RNA nucleic acid of the 5'-end region of the template RNA, or two or more linked sequences of (2) the complementary DNA nucleic acid corresponding to the 5'-end region of the template RNA, and
    decoding the sequence of the first nucleic acid by a cap analysis gene expression (CAGE) method to obtain the base sequence of the nucleic acid corresponding to the 5'-end region of the template RNA,
    wherein the unlabeled nascent RNA is isolated from a material containing an RNA associated with chromatin and is enriched for the RNA that are associated with chromatin.

2. The method according to claim 1, wherein
    in the preparing of the first nucleic acid,
    at least one of (1) the RNA nucleic acid of the 5'-end region of the template RNA or (2) the complementary DNA nucleic acid corresponding to the 5'-end region of the template RNA is prepared, and
    in the decoding, a technique based on non Amplified non Tagging Illumina Cap analysis of gene expression (nAnT-iCAGE) method is used.

3. The method according to claim 1, wherein
    in the preparing of the first nucleic acid,
    at least one of (1) the RNA nucleic acid of the 5'-end region of the template RNA or (2) the complementary DNA nucleic acid corresponding to the 5'-end region of the template RNA is prepared, and
    the preparing the first nucleic acid comprises:
        preparing a linker-added nucleic acid having a linker bound to a second nucleic acid;
        cleaving the linker-added nucleic acid with a restriction enzyme having a recognition site in the linker and a cleavage site in the second nucleic acid, and
        collecting the first nucleic acid from the obtained cleavage product,
        wherein the first nucleic acid comprises at least one of (1) the RNA nucleic acid of the 5'-end region of template RNA or (2) the complementary DNA nucleic acid corresponding to the 5'-end region of the template RNA.

4. The method according to claim 1, wherein
in the preparing of the first nucleic acid,
at least one of (1) the RNA nucleic acid of the 5'-end region of the template RNA or (2) the complementary DNA nucleic acid corresponding to the 5'-end region of the template RNA is prepared, and
the decoding comprises a template switching method.

5. The method according to claim 1, wherein
in the preparing of the first nucleic acid,
at least one of (1) the RNA nucleic acid of the 5'-end region of the template RNA or (2) the complementary DNA nucleic acid corresponding to the 5'-end region of the template RNA is prepared, and
the decoding comprises a HeliScope cap analysis of gene expression (HeliScopeCAGE) method.

6. The method according to claim 1, wherein
the nascent RNA is derived from a single cell strain or a single tissue.

7. The method according to claim 1, wherein
the nascent RNA is isolated from a complex of a template DNA and an RNA polymerase II in transcription and an RNA during synthesis.

8. The method according to claim 1, further comprising:
isolating the nascent RNA from a biological sample, wherein
the isolated nascent RNA is used as the template RNA.

9. The method according to claim 8, wherein
in the isolating of the nascent RNA,
a chromatin containing a complex of a template DNA and an RNA polymerase II in transcription and an RNA during synthesis is isolated from the biological sample, and
the RNA during synthesis contained in the complex is isolated from the chromatin as the nascent RNA.

10. A method for analyzing a DNA element, comprising:
decoding a base sequence of a nucleic acid corresponding to a 5'-end region of an RNA by the method according to claim 1, and
mapping of the DNA element that encodes the RNA to a genome location, based on the decoded base sequence information.

11. The method according to claim 10, wherein
the DNA element is identified by the mapping.

12. The method according to claim 10, further comprising:
determining an in-vivo transcriptional activity level of the DNA element from a number of overlapping decoded base sequence information mapped to the DNA element, wherein the in-vivo transcriptional activity level of the DNA element reflects the in-vivo RNA expression levels.

13. The method according to claim 12, wherein
the determined activity level of the DNA element is associated with at least one of a DNA mutation or a polymorphism in the genome.

* * * * *